(12) United States Patent
Alexander et al.

(10) Patent No.: US 6,462,201 B1
(45) Date of Patent: Oct. 8, 2002

(54) PROCESS FOR THE PRODUCTION OF N-VINYL-2-PYRROLIDONE BY VINYLATION

(75) Inventors: Anatoly Alexander, Berkeley Heights, NJ (US); Mikhail Raykh, East Brunswick, NJ (US)

(73) Assignee: ISP Investments Inc., Wilmington, DE (US)

( * ) Notice: Subject to any disclaimer, the term of this patent is extended or adjusted under 35 U.S.C. 154(b) by 146 days.

(21) Appl. No.: 09/222,197

(22) Filed: Dec. 29, 1998

(51) Int. Cl.[7] .......................................... C07D 207/267
(52) U.S. Cl. ...................................... 548/543
(58) Field of Search ......................... 548/543

(56) References Cited

U.S. PATENT DOCUMENTS 4,873,336 A * 10/1989 Liu et al. .................... 546/243

\* cited by examiner

Primary Examiner—Joseph K. McKane
Assistant Examiner—Rebecca Anderson
(74) Attorney, Agent, or Firm—Walter Katz; William J. Davis; Marilyn J. Maue

(57) ABSTRACT

A single stage process, with recirculation of reactants, is provided herein for making N-vinylpyrrolidone or N-vinyl caprolactam at a high reaction rate and selectivity and at a predetermined conversion per pass. In this process a reaction mixture is formed by saturating a non-aqueous, liquid mixture of recirculating lactam, vinyl lactam and catalyst with acetylene at low temperatures and pressures to provide a high concentration of acetylene in the liquid, pumping the saturated solution into a reactor, reacting the mixture as a single liquid phase, cooling the reaction product, withdrawing a portion of the cooled product, recirculating the rest into the reaction mixture, and continuously feeding additional lactam and catalyst therein.

6 Claims, 1 Drawing Sheet

PROCESS FOR THE PRODUCTION OF N-VINYL-2-PYRROLIDONE BY VINYLATION

BACKGROUND OF THE INVENTION

1. Field of the Invention

This invention relates to a process for making N-vinyl lactams, and, more particularly, to a single stage process, with recirculation, for making N-vinyl pyrrolidone or N-vinyl caprolactam at a high reaction rate and selectivity and at a predetermined conversion per pass.

2. Description of the Prior Art

The reaction of acetylene with a lactam in the presence of a catalytic amount of an alkali metal salt of the lactam to produce N-vinyl lactams is well known in the art. Generally, the conversion of 2-pyrrolidone, for example, is about 30 to 62%, and the selectivity is less than 90%. Attempts at higher conversions usually result in formation of non-volatile polymer residues which are difficult to separate from the desired product.

Parthasarathy et al, in U.S. Pat. No. 4,410,726, described a similar process using crown ethers (polyoxyalkylenes) as a co-catalyst in the vinylation reaction to increase the selectivity and reaction rate. However, the yield is only 70% and substantial amounts of polymer residues needed to be separated from the N-vinylpyrrolidone, unreacted 2-pyrrolidones and other by-products.

Liu et al, in U.S. Pat. No. 4,873,336, disclosed the use of potassium t-butoxide as a catalyst in the vinylation process which provided a 62% conversion and 90% selectivity.

Chu et al, in U.S. Pat. No. 5,665,889, described the use of ether oligomers or diols as a co-catalyst in an attempt to increase the yield of vinylpyrrolidone and decrease the production of by-products.

Schmidt-Radde et al, in U.S. Pat. No. 5,670,639 described a vinylation process using aqueous KOH in the vinylation.

While these and other prior art processes can increase the rate of vinylation by an increase in the reaction temperature and/or catalyst concentration, these physical changes lead to an increased amount of by-products. Furthermore, such processes are hazardous because gaseous acetylene at high pressures advantageous for high reaction rates may decompose spontaneously.

Accordingly, it is an object of this invention to provide an improved process for making N-vinyl lactam by reaction of acetylene with a lactam in the presence of a catalyst.

Another object herein is to provide a single stage process, with recirculation of the reaction mixture for making N-vinylpyrrolidone or N-vinyl caprolactam at a high reaction rate and selectivity and at a predetermined conversion per pass.

A feature of the invention is the formation of a reaction mixture by saturating a non-aqueous, liquid mixture of lactam, vinyl lactam and catalyst with acetylene at low temperatures and pressures to provide a high concentration of acetylene in the liquid.

BRIEF DESCRIPTION OF THE DRAWING

The FIGURE is a schematic illustration of the process of the invention (Example 1).

SUMMARY OF THE INVENTION

Figure 1:
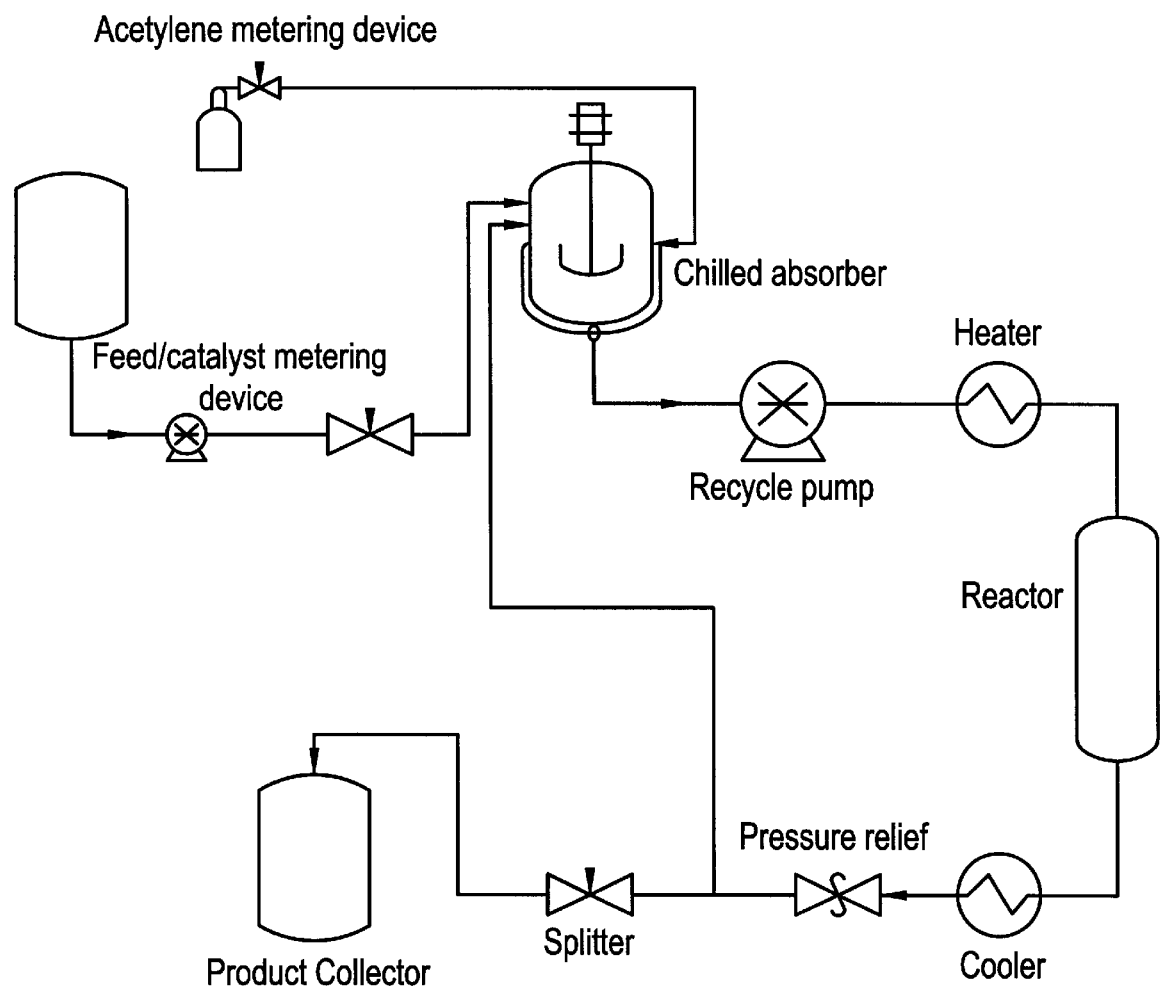

What is described herein is a single stage process, with recirculation of reaction mixture, for making an N-vinyl lactam which comprises:

(a) forming a reaction mixture by saturating a non-aqueous liquid mixture of about 10 to 99.5% by wt of a lactam selected from the group consisting of 2-pyrrolidone (2-Py) and caprolactam (CL), 0 to 90% by wt of vinyl pyrrolidone (VP) or vinyl caprolactam (VCL), 0.1 to 5% by wt of an alkali metal salt of said lactam, or equivalent thereof, as a catalyst in said process, with acetylene at a temperature of about 5 to 50° C. and at an acetylene pressure of about 5 to 100 psig, thereby to provide an acetylene concentration in said mixture of about 0.5 to 3% by wt, (b) pumping the reaction mixture at a pressure of about 200 to 3000 psig as a liquid into a reactor heated to a temperature of about 90 to 200° C., (c) reacting the mixture as a single liquid phase to produce the desired N-vinylpyrrolidone or N-vinyl caprolactam at a high reaction rate and selectivity and at a predetermined conversion, (d) cooling the reaction product, (e) withdrawing a predetermined portion of the cooled reaction product mixture, (f) recirculating the rest of the cooled reaction product into step (a), and (g) continuously feeding additional lactam and catalyst into step (a).

In preferred embodiments of the invention, in step (a), the lactam is 2-Py, the temperature is about 5–50° C., and the acetylenic pressure is about 5 to 100 psig, and, in step (b), the temperature is about 140 to 200° C. In step (a), when the lactam is CL, the temperature is about 20 to 40° C., and the acetylenic pressure is about 15 to 100 psig, and, in step (b), the temperature is about 90 to 140° C.

In a more preferred embodiment, the acetylene concentration is about 1.5% by wt.

Preferably the catalyst is the potassium salt of the lactam.

The N-vinyl lactam product and unreacted lactam usually are separated from the reaction product mixture by fractional distillation and the unreacted lactam is recycled to the reaction mixture for contact with an additional amount of catalyst.

DETAILED DESCRIPTION OF THE INVENTION

As illustrated in the FIGURE, the first step in providing the recirculating system of the invention, which is illustrated by the production of vinylpyrrolidone, is the generation of a reaction catalyst. This step is conventional in the art. Accordingly, separate streams of liquid 2-pyrrolidone and KOH are introduced into a vessel. The product is the potassium salt of 2-pyrrolidone, (catalyst) in 2-pyrrolidone (reactant) solvent. Water is removed from the catalyst-reactant solution by applying vacuum onto the vessel.

The second step of the process of the invention involves forming the reaction mixture. Accordingly, the catalyst-reactant solution is continuously pumped into a second vessel (absorber). The catalyst concentration is about 0.1 to 5% by wt. of the solution, the 2-pyrrolidone being present in an amount of about 10 to 99.9% by wt. The temperature of the solution is about 5 to 50° C. Acetylene is fed in at a pressure of about 5 to 100 psig to saturate the solution with about 0.5 to 3% by weight of acetylene.

Then, in the third step, the acetylene saturated catalyst-reactant solution is pumped into a reactor vessel heated to a temperature of about 90° to 200° C., at a pressure of about 200 to 3000 psig to keep the contents therein in the liquid state. The vinylation reaction thus occurs in a single liquid phase at a desired high reaction rate and selectivity and at a predetermined conversion.

The reaction product is substantially N-vinylpyrrolidone and unreacted 2-pyrrolidone.

The reaction product is then cooled and a portion is withdrawn. The rest is recirculated into step 2. The withdrawn reaction product then is degassed and fractionated to provide the desired N-vinylpyrrolidone product. The unreacted 2-pyrrolidone is recycled into step 1.

The recycle feature of the process of the invention is generated by recycle feeding of a major portion of the reaction product of N-vinylpyrrolidone, unreacted 2-pyrrolidone and catalyst, if any, still present in the reaction product, back into step 2.

In the preferred embodiment of the invention, where vinylpyrrolidone is the desired product, in step 1, the temperature is about 5 to 50° C., the acetylenic pressure is about 5 to 100 psig, and in step 2, the temperature is bout 140° to 200° C., and the acetylene concentration in step 2 is about 1 to 2% by wt. Where vinyl caprolactam is the desired product, in step 1, the temperature is about 20 to 50° C. and the acetylene pressure is about 15 to 100 psig, and, in step 2, the temperature is about 90 to 140° C.

In this invention, absorption of acetylene by the 2-pyrrolidone-catalyst vinylpyrrolidone solution in step 2 occurs at low pressure and low temperature, and the per-pass conversion within a recycle loop system is low. Accordingly, heat transfer in the reactor is not a problem and no high pressure gaseous acetylene is required or employed in the operation.

The overall product yield was greater than 95% of theoretical, and the space-time-yield of vinyl lactam is several times greater than in traditional continuous processes.

The invention will now be described in more detail with reference to the following example.

EXAMPLE 1

Invention Process

A bench scale recycle loop system consisting of a feed/catalyst metering device, acetylene metering device, chilled absorber, recycle high-pressure pump, recycle stream heater, reactor (100 cc), recycle stream cooler, pressure relief device, recycle stream splitter and product collector was set up as illustrated in the FIGURE and run in the following mode:

Catalyst concentration—1.3% potassium pyrrolidonate in 2-Pyrrolidone
Feed/catalyst rate—200 g/hr
Absorber temperature—15° C.
Absorber pressure—15 psig
Recycle loop pressure—600 psig
Recycle rate—60 cc/min
Reactor temperature—170° C.

After a transient period, the operation of the recycle loop system became stationary, and the following product parameters were measured:

Product rate—228 g/hr
Concentration of N-vinylpyrrolidone (GC)—51.45%
Concentration of 2-Pyrrolidone (GC)—48.00%
Concentration of volatile by-products (GC)—0.55%
Concentration of non-volatile material (Kugelrohr flash analysis)—1.42%

An overall selectivity to N-vinylpyrrolidone (VP) of 96.6% at 45% conversion was achieved. The reactor productivity was 1.15 g VP/cc-hr.

EXAMPLE 2

Comparative Run—Traditional Process

A traditional bench scale continuous reaction system consisting of a feed/catalyst metering device, acetylene metering device, high pressure stirred autoclave reactor (1 liter, Autoclave Engineers), pressure relief device and product collector was set up and run in the following mode:

Catalyst concentration—1.3% potassium pyrrolidonate in 2-Pyrrolidone
Feed/catalyst rate—200 g/hr
Reactor temperature—165° C.
Acetylene partial pressure in the reactor—100 psig
Liquid volume in the reactor—600 cc After the reaction system became stationary, the following product parameters were measured:

Product rate—231 g/hr
Concentration of N-vinylpyrrolidone (GC)—50.95%
Concentration of 2-Pyrrolidone (GC)—47.65%
Concentration of volatile by-products (GC)—1.40%
Concentration of non-volatile material (Kugelrohr flash analysis)—2.61%

The overall selectivity to N-vinylpyrrolidone (VP) was only 92.0% at 45% conversion. The reactor productivity was 0.112 g VP/cc-hr.

While the invention has been described with particular reference to certain embodiments thereof, it will be understood that changes and modifications may be made which are within the skill of the art. Accordingly, it is intended to be bound only by the following claims, in which:

What is claimed is:

1. A single stage process, with recycle, for making an N-vinyl lactam which comprises:

(a) forming a reaction mixture by saturating a non-aqueous liquid mixture of about 10 to 99.5% by wt of a lactam selected from the group consisting of 2-pyrrolidone (2-Py) and caprolactam (CL), 0 to 90% by wt of vinyl pyrrolidone (VP) or vinyl caprolactam (VCL), 0.1 to 5% by wt of an alkali metal salt of said lactam, or equivalent thereof, as a catalyst in said process, with acetylene at a temperature of about 5 to 50° C. and at an acetylene pressure of about 5 to 100 psig, thereby to provide an acetylene concentration in said mixture of about 0.5 to 3% by wt, (b) pumping the reaction mixture at a pressure of about 200 to 3000 psig into a reactor heated to a temperature of about 90 to 200° C., (c) reacting the mixture as a single liquid phase to produce the desired N-vinylpyrrolidone or N-vinyl caprolactam at a high reaction rate and selectivity and at a predetermined conversion, (d) cooling the reaction product, (e) withdrawing a predetermined portion of the cooled reaction product mixture, (f) recirculating the rest of the cooled reaction product into step (a), and (g) continuously feeding additional lactam and catalyst into step (a).

2. A process according to claim 1 wherein, in step (a), the lactam is 2-Py, the temperature is about 5–50° C. and the acetylenic pressure is about 5 to 100 psig, and, in step (b), the temperature is about 140 to 200° C.

3. A process according to claim 2 wherein the acetylene concentration is about 1.5% by wt.

4. A process according to claim 1 wherein, in step (a), the lactam is CL, the temperature is about 20 to 40° C. and the acetylenic pressure is about 15 to 100 psig, and, in step (b), the temperature is about 90 to 140° C.

5. A process according to claim 1 wherein the catalyst is the potassium salt of the lactam.

6. A process according to claim 1 wherein the N-vinylpyrrolidone product and unreacted 2-Py are separated from the reaction product mixture by fractional distillation and the unreacted 2-Py is recycled to reaction for contact with an additional amount of catalyst.

* * * * *